Figure 1:
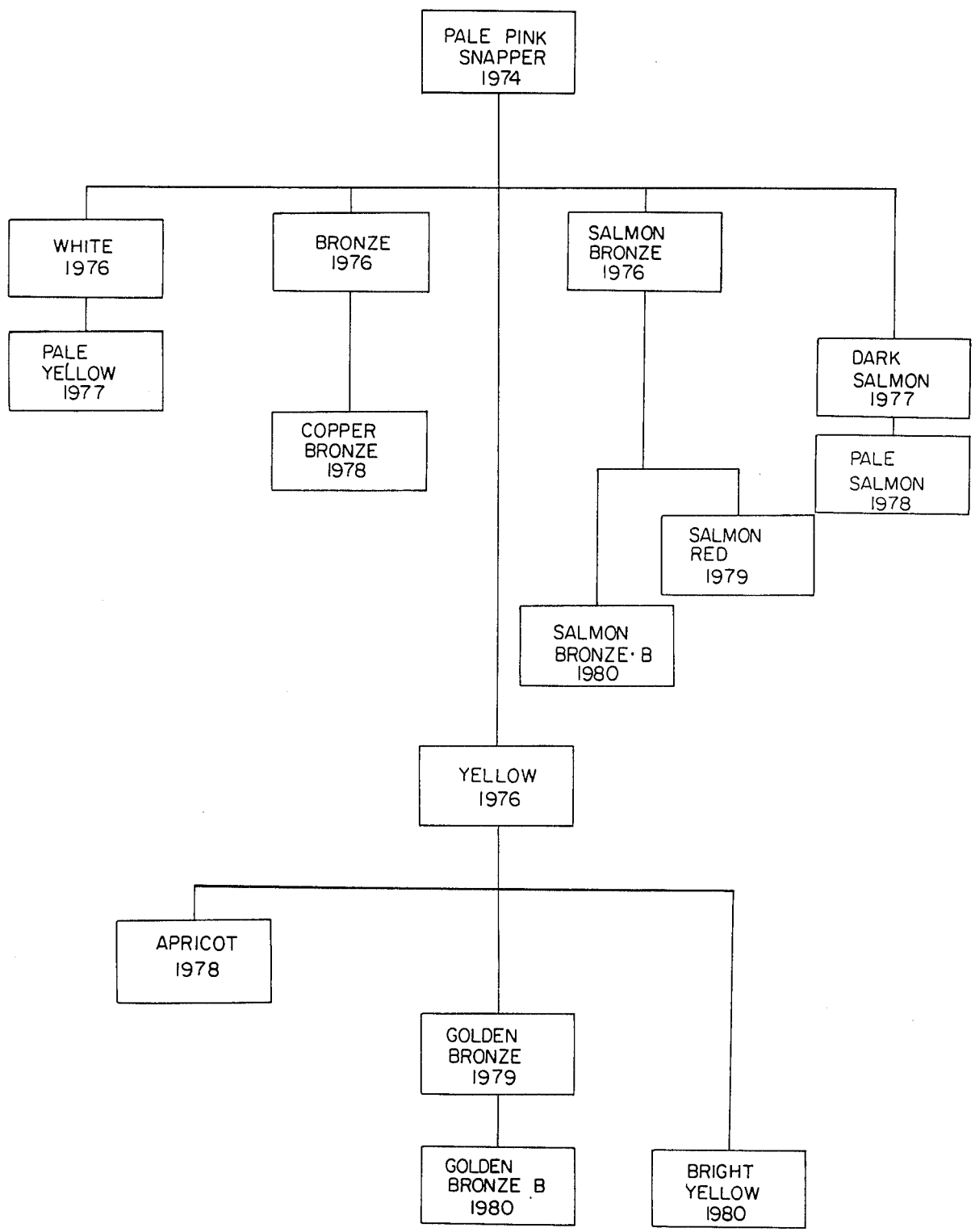
Figure 2:
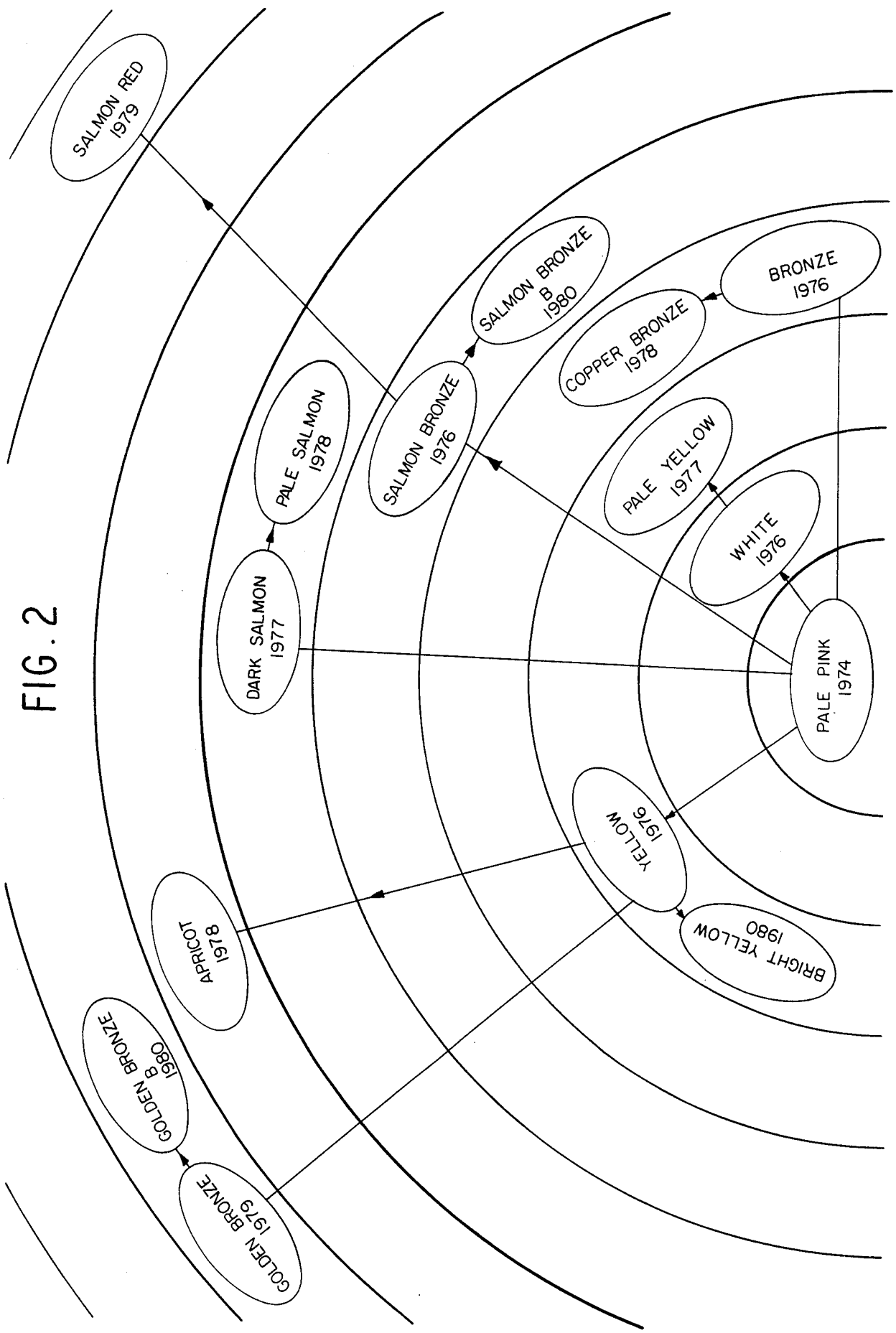
Figure 3:
Figure 4:
Figure 5:
Figure 6:
Figure 7:
Figure 8:
Figure 9:
Figure 10:
Figure 11:
Figure 12:
Figure 13:
Figure 14:
Figure 15:
Figure 16:
Figure 17:

United States Patent [19]

Sparkes

[11] Patent Number: 4,616,099

[45] Date of Patent: Oct. 7, 1986

[54] FAMILY GROUP OF SUCCESSIVE RADIATION INDUCED CHRYSANTHEMUM MUTANTS NAMED SNAPPER

[76] Inventor: A. Graham Sparkes, Hangleton Lane, Ferring, Worthing, West Sussex, England, BN12 6PP

[21] Appl. No.: 399,899

[22] Filed: Jul. 19, 1982

[51] Int. Cl.⁴ .......................... A01G 1/00; A01H 5/00
[52] U.S. Cl. .......................................... 800/1; 47/58; 47/DIG. 1; Plt./74

[58] Field of Search ................................... Plt./74-82; 47/1, 58

Primary Examiner—Robert E. Bagwill
Attorney, Agent, or Firm—Charles W. Rummler

[57] ABSTRACT

This invention comprises a family of distinctive chrysanthemum morifolium cultivars originating from a selected seedling of a genotype produced by crossbreeding and developed from the genotype by irradiation of selected clones of successive mutants induced by radiation.

18 Claims, 17 Drawing Figures
(15 of 17 Drawing(s) in Color)

FAMILY GROUP OF SUCCESSIVE RADIATION INDUCED CHRYSANTHEMUM MUTANTS NAMED SNAPPER

BACKGROUND OF THE INVENTION

The "Snapper" group of clonal chrysanthemum cultivars evolved from a breeding program initiated in 1974 at the premises of Perifleur Limited, in Sussex County, England, by A. Graham Sparkes, its Managing Director, to implement the company policy within the field of chrysanthemum cultivation. The aims and objectives of this program were to produce superior chrysanthemum cultivars that had a good response to poor light and low temperature conditions, that could be grown more efficiently and economically commensurate with good quality, fast response and low wastage for year round production, and that would also be versatile as to the range of environment in which they can perform competitively in a broad spectrum of colors.

The original or parent plant of this family resulted as a seedling of a cross between two unnamed seedling plants made by Dr. B. J. Machin, an employee of Perifleur Limited, which were selected from stock maintained for breeding purposes, namely a pale pink seedling identified by Perifleur Code 49N2×a white seedling identified by Perifleur Code 60L11, made in 1974 in greenhouse. This new seedling, when fully tested, was found to possess many of the major characteristics that were sought in the before mentioned breeding program, whereupon this plant was assigned the name "Snapper" and subsequently was given the generic name "Pale Pink Snapper", the name "Snapper" being adopted as the family name for the group of clone cultivars derived by mutation breeding begun with clones of the parent plant "Pale Pink Snapper".

Vegetative cuttings of this original plant were rooted at the premises of Perifleur Limited and the resulting plantlets were taken to Holland for Xray irradiation, a mutagenic technique known at the time to plant breeders: C. Broertjes, P. Koene and J. W. van Veen "A Mutant of a Mutant of a Mutant of a . . . Irradiation of Progressive Radiation-Induced Mutants in a Mutation-Breeding Programme with *Chrysanthemum Morifolium Ram.*" Euphytica 29 (1980) 525–530. These radiated plantlets were then returned to the premises of Perifleur Limited where they were cultivated to full flowering state, at which time the best plants were selected for propagation and commercialization. Subsequently, plantlets derived from cuttings of these selected plants were sent to Holland for irradiation and then returned to England for growth to full flowering state. Thus was begun the mutation breeding program which resulted in the family of plants herein described and illustrated by the accompanying drawings.

The selection process for determining the mutants for commercialization included various screening techniques but, in particular, the parent plant and the mutants derived therefrom were tested against a background of low temperature, a test which, it was believed, had not been carried out at that time by the breeding industry. At these low temperatures, i.e. about 45° to 60° F., it was found that chrysanthemum bud development after initiation was more rapid as compared with other varieties. At 50° F., the plants initiated buds and formed flowers normally. Moreover, and highly significant, the low temperature bud initiation and flower development occurred under conditions of poor light as in midwinter at northern latitudes. These highly significant and commercially valuable light efficiency and low temperature characteristics in all plant material derived from the original or parent plant have been subsequently confirmed by the Ministry of Agriculture, Efford Experimental Horticultural Station, at Lymington, Hampshire, England. (See Annual Report 1978)

THE DISTINCTIVE CHARACTERISTICS OF THE "SNAPPER" GROUP OF CLONE CULTIVARS

The "Snapper" group of clone cultivars herein shown and described comprises fifteen all year round, individual cut flower cultivars, each being a uniform single flower, spray type, with an eight to twelve week flowering response to photoperiodic short-day control. All cultivars of this family respond to nine weeks of short days at 60° F. and in twelve weeks of short days at 50° F. night temperatures. When light levels are high and day temperatures are relatively low (60° F. day), eight week response can be expected. It should be noted, however, that to achieve a satisfactory result in short days at 45° F. night temperatures, mother stock should be grown at 60° F. and its rooted cuttings should be grown at that temperature for three to five weeks of long days after planting out. Each cultivar in the family is of medium height, attaining as much as about 100 cm. or more when cultivated over two long-day weeks at 60° F. to full flowering maturity in the month of November on the south coast of England, with internode lengths typically below 3 cm.

1. Growth Rate and Habit

"Snapper" cultivars are distinctive in that the leaf formation in the apices is very rapid. The rate of apical leaf formation can be one leaf per day in high light conditions.

When grown as a stock plant for the purpose of producing cuttings, the cultivars of the "Snapper" family branch freely and develop shoots rapidly, a trait which results in a high cutting factor. The cuttings root readily and establish quickly when planted out. The resultant terminal shoot bears relatively small leaves and expresses buds rapidly in short-day conditions. The family has the distinct advantage of developing flowers from buds at low temperature to great effect. At 60° F., as the buds are developing into flowers, the stem and peduncle extension is considerable and above average. Further, these cultivars have been found to have a positive response to $CO_2$ low light supplementation.

2. Branching Characteristics of Vegetative Mother Plant Material

The "Snapper" family of cultivars produces cuttings in profusion, the shoots of which are of even caliber as to stem diameter and leaf size and substance.

3. Stem

Strong, wiry and upright. Stem extension continues in conjunction with flower development and ranges from about 85 cm. to about 115 cm. in length. Stem diameter ranges from about 4 to about 7 mm.

4. Foliage

The apex of each leaf is mucronate and the shape of the leaf base is rounded or acute.

In length, the leaves of "Snapper" cultivars are short to medium (small leaves about 8 cm. and large leaves around 13 cm.); in width, they are narrow to medium; and the ratio of length to width of the leaf is medium to high (the small leaf width being about 5 cm. and the large leaf width being about 8 cm.).

The leaves are of medium thickness, of fleshy texture and somewhat brittle, mediumly serrated and rather rounded. Each leaf has five distinct lobes, the lower lobes being of short to medium length. The base of the leaf sinus between the lateral lobes is round and the sinus is revolute, without a claw. The margins of the sinus between the lateral lobes are normally converging. "Snapper" cultivars in long days have natural leaf numbers between 30 and 40. The foliage tends to a dark green color with high levels of fertilizer.

5. Bud

At the stage where the flower bud is approximately 10 mm. in diameter, the involucral bracts sometimes meet over the center of the disc but at other times some of the ray florets are visible over the receptacle. Trichomes on the receptacles are infrequent and sometimes absent altogether. As the bud opens, the ray florets emerge erect before opening out laterally.

6. Flower Heads

Flowers are borne corymbioform in compound lateral clusters each of 10 to 14 flowers carried on medium length wiry peduncles. The diameter of the capitulum when plants are fully extended is generally between 7 and 10 cm., depending on the cultural conditions in force. The flower head is semi-double, with about 27 ray florets in 2 to 3 rows, each such floret having a short corolla tube.

Ray florets on "Snapper" cultivars have a textured surface and they are arranged in composite-single form. In shape, they are generally oblong and in cross-section, the form is convex. The keel number for the ray floret is normally two. The outer florets are in length short (average 35 mm.) to medium (average 40 mm.); and in width medium (average 12 mm.) to broad (average 13 mm.). On the longitudinal axis, the majority of ray florets are reflexing at the tip.

The involucral bracts are generally arranged in five rows or less. None are observed among the disc florets. The bracts are ovate in shape, colored green, and some have translucent margins.

The disc, when fully open, is of medium diameter (average 20 mm.), green before dehiscence and yellowing on dehiscence. The disc florets are numerous, massed and sometimes clearly visible at Stage 3 (according to UPOV Guidelines in TG/26/4 Nov. 14, 1979) of flower head development. They are of medium length (inclusive of ovary and anthers when ripe) and tubular in shape.

The receptacle takes the form of raised conical as reflected in the shape of the disc.

Both ray and disc florets have styles. Pollen on the anthers varies from none to abundant.

The flower resists shatter and its fragrance is typical chrysanthemum.

7. Persistence

"Snapper" inflorescence persists from 10 to 14 days on a plant. When harvested in optimum conditions, "Snapper" cultivars have an excellent vase life which can be in excess of three weeks.

8. Chromosome Count

The chromosome count for all cultivars in the "Snapper" family is 54. A specific chromosomal characteristic of the "Snapper" cultivars is to be found in the fact that one chromosome is telocentric.

DESCRIPTION OF THE DRAWINGS AND PHOTOGRAPHS

The file of this patent contains at least one drawing executed in color to meet the requirements of 35 U.S.C. 112. Copies of this patent with color drawing(s) will be provided by the Patent and Trademark Office upon request and payment of the necessary fee.

Sheet 1 is a chart showing the lineal descendants, by mutation breeding, of the original or parent plant "Pale Pink Snapper".

Sheet 2 is a chart of the mutation descendants of the parent plant "Pale Pink Snapper" arranged in successive circles about a common center according to color and within The R.H.S. Colour Chart definitions.

Sheet 3 is a full color photograph of the hybrid parent "Pale Pink Snapper".

Sheet 4 is a full color photograph of the cultivar "White Snapper".

Sheet 5 is a full color photograph of the cultivar "Bronze Snapper".

Sheet 6 is a full color photograph of the cultivar "Salmon Bronze Snapper".

Sheet 7 is a full color photograph of the cultivar "Yellow Snapper".

Sheet 8 is a full color photograph of the cultivar "Dark Salmon Snapper".

Sheet 9 is a full color photograph of the cultivar "Pale Yellow Snapper".

Sheet 10 is a full color photograph of the cultivar "Copper Bronze Snapper".

Sheet 11 is a full color photograph of the cultivar "Apricot Snapper".

Sheet 12 is a full color photograph of the cultivar "Pale Salmon Snapper".

Sheet 13 is a full color photograph of the cultivar "Golden Bronze Snapper".

Sheet 14 is a full color photograph of the cultivar "Salmon Red Snapper".

Sheet 15 is a full color photograph of the cultivar "Bright Yellow Snapper".

Sheet 16 is a full color photograph of the cultivar "Dark Golden Bronze Snapper".

Sheet 17 is a full color photograph of the cultivar "Dark Salmon Bronze Snapper".

THE FOLLOWING IS A CHRONOLOGICAL LISTING OF THE SERIES OF MUTATION INDUCED CULTIVARS COMPRISING THE "SNAPPER" FAMILY ACCORDING TO SHEETS 1 AND 2 OF THE DRAWINGS

A. "Pale Pink Snapper" is a selected seedling of Perifleur Code 49N2×Perifleur Code 60N11.

B. All others of the family are products of mutation breeding begun by irradiation of clones of the generic base ("Pale Pink Snapper" 1974), all being identical and unaltered descendants except to the extent that irradiation affects their genetic constitution. These are as follows:
  I. "White", "Bronze", "Yellow" and "Salmon Bronze" are selected 1976 radiation induced mutants of clones of "Pale Pink Snapper".
  II. "Dark Salmon" is a selected 1977 radiation induced mutant of a "Pale Pink Snapper" clone; and "Pale Yellow" is a selected 1977 radiation induced mutant of a clone of "White" (1976).
  III. "Copper Bronze" is a 1978 radiation induced mutant of a clone of "Bronze" (1976); "Apricot" is a 1978 radiation induced mutant of a clone of "Yellow" (1976); and "Pale Salmon" is a 1978 radiation induced mutant of a "Dark Salmon" clone.

IV. "Golden Bronze" is a 1979 radiation induced mutant of a clone of "Yellow" (1979); and "Salmon Red" is a 1979 radiation induced mutant of a clone of "Salmon Bronze" (1976).

V. "Dark Salmon Bronze" is a 1980 radiation induced mutant of a clone of "Salmon Bronze" (1976); "Dark Golden Bronze" is a 1980 radiation induced mutant of a clone of "Golden Bronze" (1979); and "Bright Yellow" is a 1980 radiation induced mutant of a clone of "Yellow" (1976).

THE FOLLOWING ARE DETAILED DESCRIPTIONS OF THE SEVERAL MEMBERS OF THE "SNAPPER" FAMILY OF CLONAL CULTIVARS. COLOR DESIGNATIONS ARE ACCORDING TO THE R.H.S. COLOUR CHART OF THE ROYAL HORTICULTURAL SOCIETY (RHS)

These measurements were obtained from randomly selected plants on Apr. 6, 1982, growing in a greenhouse at the premises of Perifleur Limited, Hangleton Lane, Ferring, Worthing, West Sussex, England.

The plants from which the measurements were obtained had been planted in that greenhouse on Dec. 15, 1981. During growth, the plants were subjected to four weeks of long days and nine weeks of short days. The short days began on Jan. 16, 1982, and continued up to flowering. Night break lighting was used to give the long days. The short days were of natural day length.

The base dressing and liquid feed applied to the plants comprises a composition of:
Triple Super-Phosphate, applied at 0.6 Kg/m$^2$,
Nitrate of Potash, applied at 0.7 Kg/m$^2$, and
Calcium Nitrate, applied at 0.6 Kg/m$^2$;
this base dressing being supplemented by liquid feed as may be desired for the particular growing environment.

The following are light measurements for the relevant period recorded by the Glasshouse Crops Research Institute, Worthing Road, Rustington, Littlehampton, West Sussex, England.

| Week ending | | | | | |
|---|---|---|---|---|---|
| 20 Dec | 16.75 (MJm-2) | 28 Jan | 24.11 (MJm-2) | 4 Mar | 41.38 (MJm-2) |
| 27 Dec | 13.04 (MJm-2) | 4 Feb | 27.58 (MJm-2) | 11 Mar | 81.58 (MJm-2) |
| 7 Jan | 12.64 (MJm-2) | 11 Feb | 26.2 (MJm-2) | 18 Mar | 72.61 (MJm-2) |
| 14 Jan | 23.88 (MJm-2) | 18 Feb | 26.49 (MJm-2) | 25 Mar | 83.67 (MJm-2) |
| 21 Jan | 21.16 (MJm-2) | 25 Feb | 36.6 (MJm-2) | 1 Apl | 97.53 (MJm-2) |
| | | | | 8 Apl | 83.28 (MJm-2) |

The latitude of Perifleur Limited's premises at Hangleton Lane is 50°-40' N. (Fifty degrees forty minutes north)

Between Mar. 17 and Mar. 20, 1982, the plants from which the measurements were obtained came into full flower. Throughout the period, from planting to full flowering, the night temperature in the greenhouse was constant at 60° F.

The plants from which the measurements were obtained were taken from the middle of the flower bed.

The flower stem length was measured from ground level to the highest point on the flowers. The stem diameter was measured at a point 12 inches up the stem from ground level.

Measurements were obtained from two leaves, one leaf "A" being taken from the base of the lower peduncle and the other leaf "B" being taken from a point 12 inches up the stem from ground level.

The ray floret data was taken from the outer, lower ring of ray florets.

Capitulum was understood to be as in UPOV Guidelines TG/26/4, Character 29.

Depth and diameter were measured when the flower was fully open. The flower colors stated relate to the ray florets.

| 1. PALE PINK SNAPPER (The Hybrid Parent) | |
|---|---|
| Origin: | Seedling |
| Parentage: | Female seed parent - Perifleur Code 49N2. Male pollen parent - Perifleur Code 60N11. |
| Classification | Chrysanthemum Morifolium Ramat |
| Form: | Perennial herbaceous bush. |
| Flower Stem: | |
| | Length - 99 cm. |
| | Diameter - 6 mm. |
| Growth: | Terminal; vigorous and stiffly upright. |
| Branching: | Freely branching with rapid development of shoots which are erect and do not spread. The terminal shoot bears relatively small leaves and develops and expresses buds rapidly under short-day conditions. |
| Foliage: | |
| Quantity: | Medium with very rapid leaf formation in the apices, leaf formation being as much as one leaf per day in high-light conditions with a natural leaf number of 34. |
| Size of Leaf: | |
| | A - Length - 118 mm. Width - 78 mm. |
| | B - Length - 138 mm. Width - 90 mm. |
| Shape of Leaf: | Each leaf has five lobes, the lower lobes being of medium length. The base of the leaf sinus between the lateral lobes is round and the sinus is revolute without a claw. |
| Color: | Dark Green RHS 137B. |
| Venation: | Leaves are bi-pinnately veined. |
| Petioles: | Length - About 2.5 cm. |
| Stem Color: | RHS 143D |

THE BUD STAGE

| | |
|---|---|
| Form: | Globular |
| Size: | About 14 mm. in diameter when the phyllaries are just breaking open. Depth - About 8 mm. |
| Opening Rate: | Medium. About 7 days from color to maturity. |
| Color of Ray Florets: | When bracts first separate: RHS 75D. When florets begin to unfurl: Outer side (under side of opened flower): RHS 75D. Inner side (top side of opened flower): RHS 75C. |
| Involucral Bracts: | |
| Bracts: | Small, convex in cross-section with round tips. About 30 in number. |
| Color: | Inside and outside: RHS 137B. |
| Involucre: | |
| Shape: | Flat |
| Diameter: | Slightly greater than disc. |
| Peduncle: | Erect and averaging 12-15 cm. in length. |

-continued

1. PALE PINK SNAPPER (The Hybrid Parent)

| | |
|---|---|
| cle: | |
| Color: | RHS 137D |
| Surface Aspect: | Pubescent |

THE FLOWER STAGE

| | |
|---|---|
| Response | 9-week response group at 60° F. night temperature, flowering freely all year round with photoperiod control. |
| Bloom: | |
| Flower Type: | Daisy Capitulum. |
| Borne: | In corymbiform-spray clusters. |
| Size: | Medium. About 70 to about 80 mm. in diameter when fully open and about 1.4 cm. in depth. |
| Shape: | Cup-shaped when bloom first opens, becoming flat with reflexing tips as flower matures. |
| Florets: | About 23 to 30 ray florets, arranged in composite form, and about 260 disc florets. |
| Ray Florets Shape: | Linear with rounded to beaked tip about 40 mm. long and about 15 mm. wide; convex in cross-section with a keel number of 2 and reflexing on the longitudinal axis. |
| Ray Florets: | |
| Color: | When flowers are expanding cup-shaped: |
| | Outer side - 75D. |
| | Inner side - 75C. |
| | When flowerhead is fully matured and blown: |
| | side - 75D. |
| | Disc color - 144B |
| Texture: | Velvet, firm and smooth. |
| Appearance: | Velvety |
| Discoloration: | Disc color at dehiscence - 14C. |
| Peduncle: | Sturdy and upright, about 14 cm. long. |
| Color: | 137B |
| Persistence: | Florets hang on and dry. |
| Lasting Quality: | As cut flowers, vase life can be about three weeks depending on environmental conditions. |

REPRODUCTIVE ORGANS

| | |
|---|---|
| Disc: | |
| Stamens: | About 260. |
| Anthers: | Size - 0.75 mm. |
| Color: | Yellow |
| Filaments: | About 4.5 mm. long. Pale green in color. |
| Pollen: | Golden yellow in color. |
| Pistils: | Number - About 260. |
| Styles: | About 5 mm. long, pale green in color. |
| Stigmas: | Yellow in color. |
| Ray Florets: | |
| Pistils: | One for each ray floret, 10 mm. long and green in color. |
| Styles: | Golden yellow in color. |
| Stigmas: | Diameter - About 5 mm. |
| Calyx: | Undeveloped, fringe on disc and ray florets, no pappus. |
| Chromosome Count: | 54, a specific chromosomal characteristic being the fact that one chromosome is telocentric. |

Each of the following is a mutation descendant of PALE PINK SNAPPER and conforms with the general description of the "Snapper" family but has the following specific characteristics:

2. WHITE SNAPPER (1976)

| | |
|---|---|
| Capitulum: | Diameter - 80 mm.; Depth 19 mm. |
| Flower Stem: | Length - 93 cm.; Diameter - 6 mm. |
| Color: | 146A |
| Bud: | Color when bracts first divide - 155D. |
| Ray Florets: | |
| | Shape - Convex. |
| | Tip - Rounded. |
| Color: | When flowers are expanding: |
| | Upper outer side - 155D. |
| | Underside inner side - 155D. |
| | When flowerhead is fully matured and blown: |
| | Under inner side - 155D. |
| Disc Color: | 144B. At dehiscence - 14B. |
| Leaves: | |
| | A - Length 120 mm. Width - 67 mm. |
| | B - Length 120 mm. Width - 87 mm. |
| Shape: | 5 lobed, rounded. |
| Color: | 137A |

3. BRONZE SNAPPER (1976)

| | |
|---|---|
| Capitulum: | Diameter - 80 mm.; Depth - 17 mm. |
| Flower Stem: | Length - 87 cm.; Diameter - 7 mm. |
| Color: | 146D |
| Bud: | Color when bracts first divide - 167B. |
| Ray Florets: | |
| | Shape - Convex. |
| | Tip - Rounded. |
| Color: | When flowers are expanding: |
| | Outer side - 163C. |
| | Inner side - 13C. |
| | When flowerhead blown: |
| | Upper side - 11B. |
| Disc Color: | 144B. At dehiscence - 14C. |
| Leaves: | |
| | A - Length - 114 mm. Width - 70 mm. |
| | B - Length - 122 mm. Width - 79 mm. |
| Shape: | 5 lobed, rounded. |
| Color: | 147A |

4. SALMON BRONZE SNAPPER

| | |
|---|---|
| Capitulum: | Diameter - 80 mm. Depth - 18 mm. |
| Flower Stem: | Length - 99 cm. Diameter - 6 mm. |
| Color: | 146B |
| Bud: | Color when bracts first divide - 173C overlaid 173D. |
| Ray Florets: | |
| | Shape - Convex. |
| | Tip - Pointed. |
| Color: | When flowers are expanding: |
| | Outer side - 11C. |
| | Inner side - 162B overlaid 46A. |
| | When flowerhead blown: |
| | Inner side - 161C overlaid 182C. |
| Disc Color: | 144B. At dehiscence - 14C. |
| Leaves: | |
| | A - Length - 110 mm. Width - 64 mm. |
| | B - Length - 137 mm. Width - 81 mm |
| Shape: | 5 lobed |
| Color: | 137A |

5. YELLOW SNAPPER

| | |
|---|---|
| Capitulum: | Diameter - 80 mm. Depth - 19 mm. |
| Flower Stem: | Length - 94 cm. Diameter - 6 mm. |
| Color: | 137A |
| Bud: | Color when bracts first divide - 7D. |
| Ray Florets: | |
| | Shape - Convex. |

-continued

5. YELLOW SNAPPER

| | |
|---|---|
| Color: | Tip - Pointed |
| | When flowers are expanding: |
| | Outer side - 8B. |
| | Inner side - 7B. |
| | When flowerhead blown: |
| | Upper side - 4D. |
| Disc Color: | 144B. At dehiscence - 14C. |
| Leaves | |
| | A - Length - 116 mm. Width - 73 mm. |
| | B - Length - 148 mm. Width - 79 mm. |
| Shape: | 5 lobed rounded. |
| Color: | 146A |

6. DARK SALMON SNAPPER

| | |
|---|---|
| Capitulum: | Diameter - 75 mm. Depth - 16 mm. |
| Flower Stem: | Length - 112 cm. Diameter - 6 mm. |
| Color: | 146B |
| Bud: | Color when bracts first divide - 174C overlaid 171D. |
| Ray Florets: | |
| | Shape - Convex. |
| | Tip - Pointed. |
| Color: | When flowers are expanding: |
| | Outer side - 11C with faint red tones. |
| | Inner side - 11C overlaid 181C. |
| | When flowerhead blown: |
| | Upper side - 159B overlaid 186A. |
| Disc Color: | 144B. At dehiscence - 14C. |
| Leaves: | |
| | A - Length - 92 mm. Width - 62 mm. |
| | B - Length - 116 mm. Width - 80 mm. |
| Shape: | 5 lobed, rounded. |
| Color: | 137A |

7. PALE YELLOW SNAPPER

| | |
|---|---|
| Capitulum: | Diameter - 75 mm. Depth - 19 mm. |
| Flower Stem: | Length - 87 cm. Diameter - 4 mm. |
| Color: | 137D |
| Bud: | Color when bracts first divide - 4D. |
| Ray Florets: | |
| | Shape - Convex. |
| | Tip - Rounded/beaked. |
| Color | When flowers are expanding: |
| | Outer side - 4D. |
| | Inner side - 4C. |
| | When flowerhead blown: |
| | Upper side - 5D. |
| Disc Color: | 144B At dehiscence - 13B. |
| Leaves: | |
| | A - Length - 77 mm. Width - 48 mm. |
| | B - Length - 96 mm. Width - 62 mm. |
| Shape: | 5 lobed, rounded. |
| Color: | 146A |

8. COPPER BRONZE SNAPPER

| | |
|---|---|
| Capitulum: | Diameter - 85 mm. Depth - 19 mm. |
| Flower Stem: | Length - 91 cm. Diameter - 6 mm. |
| Color: | 146C |
| Bud: | Color when bracts first divide - 168C overlaid 163C. |
| Ray Florets: | |
| | Shape - Convex. |
| | Tip - Pointed. |
| Color: | When flowers are expanding: |
| | Outer side - 10B overlaid 46A. |
| | Inner side - 13B overlaid 46A. |

8. COPPER BRONZE SNAPPER

| | |
|---|---|
| | When flowerhead blown: |
| | Upper side - 12D overlaid 182A. |
| Disc Color: | 144B. At dehiscence - 14C. |
| Leaves: | |
| | A - Length - 110 mm. Width - 75 mm. |
| | B - Length - 130 mm. Width - 76 mm. |
| Shape: | 5 lobed, rounded. |
| Color: | 137A |

9. APRICOT SNAPPER

| | |
|---|---|
| Capitulum: | Diameter - 85 mm. Depth - 20 mm. |
| Flower Stem: | Length - 106 cm. Diameter - 7 mm. |
| Color: | 137A |
| Bud: | Color when bracts first divide - 31D overlaid 11C. |
| Ray Florets: | |
| | Shape - Convex. |
| | Tip - Pointed. |
| Color: | When flowers are expanding: |
| | Outer side - 161A. |
| | Inner side - 163B overlaid 46A. |
| | When flowerhead blown: |
| | Upper side 4C lightly overlaid with 70A. |
| Disc Color: | 144B. At dehiscence - 14C. |
| Leaves: | |
| | A - Length - 110 mm. Width - 68 mm. |
| | B - Length - 146 mm. Width - 82 mm. |
| Shape: | 5 lobed, rounded. |
| Color: | 146A |

10. PALE SALMON SNAPPER

| | |
|---|---|
| Capitulum: | Diameter - 85 mm. Depth - 22 mm. |
| Flower Stem: | Length - 97 cm. Diameter - 6 mm. |
| Color: | 139C |
| Bud: | Color when bracts first divide - 27A. |
| Ray Florets: | |
| | Shape - Convex. |
| | Tip - Rounded/beaked. |
| Color: | When flowers are expanding: |
| | Outer side - 11C. |
| | Inner side - 25D. |
| | When flowerhead blown: |
| | Upper side - 23D. |
| Disc Color: | 144B. At dehiscence - 14C. |
| Leaves: | |
| | A - Length - 100 mm. Width - 65 mm. |
| | B - Length - 109 mm. Width - 69 mm. |
| Shape: | 5 lobed, rounded. |
| Color: | 146A |

11. GOLDEN BRONZE SNAPPER

| | |
|---|---|
| Capitulum: | Diameter - 78 mm. Depth - 20 mm. |
| Flower Stem: | Length - 96 c. Diameter - 5 mm. |
| Color: | 139C |
| Bud: | Color when bracts first divide - 22A. |
| Ray Florets: | |
| | Shape - Convex. |
| | Tip - Rounded/beaked. |
| Color: | When flowers are expanding: |
| | Outer side - 13C. |
| | Inner side - 23B. |
| | When flowerhead blown: |
| | Upper side - 22B. |
| Disc Color: | 144B. At dehiscence - 14C. |
| Leaves: | |
| | A - Length - 92 mm. Width - 60 mm. |
| | B - Length - 125 mm. Width - 71 mm. |
| Shape: | 5 lobed, rounded. |

-continued

| 11. GOLDEN BRONZE SNAPPER | |
|---|---|
| Color: | 147A |

| 12. SALMON RED SNAPPER | |
|---|---|
| Capitulum: | Diameter - 80 mm. Depth - 20 mm. |
| Flower Stem: | Length - 85 cm. Diameter - 6 mm. |
| Color: | 146B |
| Bud: | Color when bracts first divide - 35C overlaid 181C. |
| Ray Florets: | |
| | Shape - Convex. |
| | Tip - Rounded/beaked. |
| Color: | When flowers are expanding: |
| | Outer side - 34C. |
| | Inner side - 34B. |
| | When flowerhead blown: |
| | Upper side - 31B. |
| Disc Color: | 144B. At dehiscence - 15C. |
| Leaves: | |
| | A - Length - 95 mm. Width - 55 mm. |
| | B - Length - 107 mm. Width - 86 mm. |
| Shape: | 5 lobed, rounded. |
| Color: | 137A |

| 13. BRIGHT YELLOW SNAPPER | |
|---|---|
| Capitulum: | Diameter - 80 mm. Depth - 18 mm. |
| Flower Stem: | Length - 102 cm. Diameter - 6 mm. |
| Color: | 148B |
| Bud: | Color when bracts first divide - 12A overlaid 12B. |
| Ray Florets: | |
| | Shape - Convex. |
| | Tip - Rounded/beaked. |
| Color: | When flowers are expanding: |
| | Outer side - 8B. |
| | Inner side - 9A. |
| | When flowerhead blown: |
| | Upper side - 14C. |
| Disc Color: | 144B. At dehiscence - 14C. |
| Leaves: | |
| | A - Length - 114 mm. Width - 70 mm. |
| | B - Length - 120 mm. Width - 71 mm. |
| Shape: | 5 lobed, rounded. |
| Color: | 146A |

| 14. DARK GOLDEN BRONZE SNAPPER | |
|---|---|
| Capitulum: | Diameter - 85 mm. Depth - 21 mm. |
| Flower Stem: | Length - 99 cm. Diameter - 6 mm. |
| Color: | 147C |
| Bud: | Color when bracts first divide - 26B overlaid 22B. |
| Ray Florets: | |
| | Shape - Convex. |
| | Tip - Rounded/beaked. |
| Color: | When flowers are expanding: |
| | Outer side - 13B. |
| | Inner side - 24B. |
| | When flowerhead blown: |
| | Upper side - 24C. |
| Disc Color: | 144B. At dehiscence - 14C. |
| Leaves: | |
| | A - Length - 104 mm. Width - 59 mm. |
| | B - Length - 123 mm. Width - 76 mm. |
| Shape: | 5 lobed, rounded. |
| Color: | 147A |

| 15. DARK SALMON BRONZE SNAPPER | |
|---|---|
| Capitulum: | Diameter - 85 mm. Depth - 22 mm. |
| Flower Stem: | Length - 107 cm. Diameter - 7 mm. |
| Color: | 139D |
| Bud: | Color when bracts first divide - 26C overlaid 31D. |
| Ray Florets: | |
| | Shape - Convex. |
| | Tip - Rounded/beaked. |
| Color: | When flowers are expanding: |
| | Outer side - 19C. |
| | Inner side - 26C. |
| | When flowerhead blown: |
| | Upper side - 26D. |
| Disc Color: | 144B. At dehiscence - 14C. |
| Leaves: | |
| | A - Length - 106 mm. Width - 53 mm. |
| | B - Length - 140 mm. Width - 77 mm. |
| Shape: | 5 lobed, rounded. |
| Color: | 137A |

Deposit of material for each of the above described cultivars has been made at the Plant Variety Rights Office at Cambride, England, and the following chart shows date and deposit number for each variety:

| Name | Date | Deposit Number |
|---|---|---|
| PALE PINK SNAPPER | 10/12/76 | AFP 15/361 |
| WHITE SNAPPER | 4/21/78 | AFP 15/561 |
| BRONZE SNAPPER | 4/21/78 | AFP 15/560 |
| SALMON BRONZE SNAPPER | 5/11/79 | AFP 15/766 |
| YELLOW SNAPPER | 5/11/79 | AFP 15/763 |
| DARK SALMON SNAPPER | 5/11/79 | AFP 15/770 |
| PALE YELLOW SNAPPER | 5/26/81 | AFP 15/1061 |
| COPPER BRONZE SNAPPER | 5/11/79 | AFP 15/765 |
| APRICOT SNAPPER | 5/11/79 | AFP 15/767 |
| PALE SALMON SNAPPER | 5/26/81 | AFP 15/1060 |
| GOLDEN BRONZE SNAPPER | 5/11/79 | AFP 15/769 |
| SALMON RED SNAPPER | 4/27/81 | AFP 15/1052 |
| BRIGHT YELLOW SNAPPER | 10/10/80 | AFP 15/978 |
| DARK GOLDEN BRONZE SNAPPER | | AFP 15/1520 |
| DARK SALMON BRONZE SNAPPER | | AFP 15/1521 |

Particular advantages of the "Snapper" cultivars reside in the fact that they have the ability to develop buds to full flower expression which are initiated and develop at temperatures as low as 50° F. and in poor light. This characteristic is very important in northern latitudes not only because of the depleting effect of poor light on quantity and quality of flowers, but because of the increasingly important economic aspect of a reduced energy requirement. This characteristic is enhanced by the "Snapper" cultivars having an efficient photoresponsive leaf, reacting very favorably to supplementary $CO_2$ in low light conditions with a resultant improvement in overall growth quality.

A reduced energy requirement also results when the cultivars are grown at the traditional temperature of 60° F. because their flowering response in short days is fast, being eight to nine weeks.

"Snapper" cultivars grown at stock plants show growth characteristics of great commercial significance not only because the cutting factor is high, but also because individual shoots are more standardized as to caliber, the importance of this particular characteristic being that there are less problems in the grading of cuttings and the resulting flower performance is also standardized and even.

Also, the "Snapper" cultivars are capable of producing substantial numbers of flowers in the spray form especially in the wintertime. "Snapper" cultivars have a high percentage cut out of quality and yield with a waste factor that is minimal.

The important characteristic of a green disc contributes to an excellent flower expression. Where "Snapper" cultivars are grown as pot plants and growth regulants are suitably applied, the resulting effect is a very attractive, ornamental pot plant.

The broad color spectrum of the "Snapper" family of cultivars simplifies the programming of year round production and likewise reflects favorably on the economy of producing cuttings from stock plants, thus obviating the problem of growing a range of different hybrid cultivars in order to provide a comprehensive combination of colors for a balanced year round flowering program.

PRIOR ART DISTINGUISHED

Of the many commercial cultivars known to Perifleur Limited, the most similar existing commercially available cultivars are of the "Marble" family.

The "Snapper" cultivars were compared with "Coral Marble", a member cultivar of the "Marble" family, at the premises in England of Perifleur Limited on Apr. 19, 1982. "Coral Marble" was grown in the same greenhouse as the "Snapper" cultivars in a manner designed to facilitate a valid comparison between the two.

The comparison disclosed the following differences between "Coral Marble" and the "Snapper" cultivars that are the subject matter of this patent application:

The shape of the disc in "Snapper" cultivars tends to be more pointed than the disc in "Coral Marble".

The disc floret ovules on "Coral Marble" are, when the flower is fully matured and blown, longer than those on the "Snapper" cultivar in the same condition and the "Coral Marble" disc is larger in diameter.

The number and their pronouncement of ray floret keels differs from that in "Coral Marble".

Juvenile ray floret curling (an undesirable trait) is more pronounced in "Coral Marble" than in the "Snapper" cultivars.

The ray florets on "Coral Marble" emerge in the shape of a quill, develop into an open quill and when fully extended the edges of the corolla tend to roll back. The ray florets in "Snapper" cultivars emerge upright in spatulate quill form and then open outwards without any noticeable tendency for the corolla to roll back at the edges.

When fully expanded, the ray florets in the outer, lower ring of florets on "Coral Marble" are longer and more pointed than florets in the same position on "Snapper" cultivars, the florets on which latter in that position are broader and shorter. Several "Snapper" cultivars have a 'beak' at the ray floret tip.

Bracts from the involucre are sometimes present among the disc florets of "Coral Marble".

The angle of the peduncle with the stem is narrower (more acute) on "Snapper" cultivars.

The leaf lobes of "Snapper" cultivars are more rounded than those of "Coral Marble". The leaves of "Coral Marble" are bigger, more serrated, more obviously pointed at the lobe tip, and have the overall appearance of 'leaping flames'. The indentations are sharper and deeper.

The leaves on "Snapper" cultivars are free of pits and lesions, unlike the leaves of "Coral Marble" which tend to pit, go brown and scar badly.

Whereas "Coral Marble" will initiate buds at below 60° Fahrenheit in northern latitudes in wintertime, the inflorescence which develops is generally below commercially acceptable standards, unlike the commercially acceptable inflorescence which develops on the "Snapper" cultivars under the same conditions. "Coral Marble" is essentially a summer cultivar, flowering between April and September. The "Snapper" cultivars have all-year-round potential.

The following is a chart of principal measurements pertaining to the herein described members of the "Snapper" family of clonal cultivars.

| | | | Leaves | | | | | | | |
| | Flower Stem | | At Peduncle Base | | 12" Up Stem | | Ray Floret | | Capitulum Fully Open | |
| SNAPPER | L cm | Dia. mm | L mm | W mm | L mm | W mm | L mm | W mm | Depth mm | Dia. mm |
| --- | --- | --- | --- | --- | --- | --- | --- | --- | --- | --- |
| 1. Pale Pink | 99 | 6 | 118 | 78 | 138 | 90 | 40 | 15 | 14 | 70–80 |
| 2. White | 93 | 6 | 120 | 67 | 120 | 87 | 40 | 15 | 19 | 80 |
| 3. Bronze | 87 | 7 | 114 | 70 | 122 | 79 | 38 | 16 | 17 | 80 |
| 4. Salmon Bronze | 99 | 6 | 110 | 64 | 137 | 81 | 40 | 14 | 18 | 80 |
| 5. Yellow | 94 | 6 | 116 | 73 | 148 | 79 | 41 | 17 | 19 | 80 |
| 6. Dark Salmon | 112 | 6 | 92 | 62 | 116 | 80 | 40 | 16 | 16 | 75 |
| 7. Pale Yellow | 87 | 4 | 77 | 48 | 96 | 62 | 37 | 15 | 19 | 75 |
| 8. Copper Bronze | 91 | 6 | 110 | 75 | 130 | 76 | 41 | 17 | 19 | 85 |
| 9. Apricot | 106 | 7 | 110 | 68 | 146 | 82 | 40 | 16 | 20 | 85 |
| 10. Pale Salmon | 97 | 6 | 100 | 65 | 109 | 69 | 43 | 16 | 22 | 85 |
| 11. Golden Bronze | 96 | 5 | 92 | 60 | 125 | 71 | 41 | 16 | 20 | 78 |
| 12. Salmon Red | 85 | 6 | 95 | 55 | 107 | 86 | 38 | 11 | 20 | 80 |
| 13. Bright Yellow | 102 | 6 | 114 | 70 | 120 | 71 | 41 | 17 | 18 | 80 |
| 14. Dark Golden Bronze | 99 | 6 | 104 | 59 | 123 | 76 | 46 | 18 | 21 | 85 |
| 15. Dark Salmon Bronze | 107 | 7 | 106 | 53 | 140 | 77 | 44 | 17 | 22 | 85 |

I claim:

1. A chrysanthemum plant of the *morifolium ramat* species having a rapid growth rate reaching a height ranging from about 85 cm. to about 112 cm. within substantially two long-day weeks at 60° F. with internode lengths approximately 30 mm. and a stem diameter of from 4 to 7 mm.; a reliable 8 to 12 weeks short-day response in winter light and 45° to 60° night temperature, this plant having a continuous year-round flowering capability producing a profusion of flowers borne in compound lateral clusters; each cluster comprising 10 to 14 flowers each having a newly-opened diameter of 70 to 80 mm., a fully expanded diameter of 70 to 90 mm., florets comprising approximately 23 to 30 ray florets of about 35 to 45 mm. long and about 10 to 20 mm. wide and approximately 220–260 disc florets, the disc florets being of a green color (R.H.S. 144B) before dehiscence and yellowing on dehiscence, the average disc diameter being about 20 mm.; this plant being further distinguished by its high sensitivity and responsiveness to $CO_2$ and supplementary light, with bud and flower development at 50° F. or less, by its very rapid apical leaf formation with as much as one leaf per day in high light, by its free branching with rapid and erect shoot development, by having a chromosome count of 54 of which one chromosome is telocentric; and wherein the color of the ray florets is one of the group consisting of the R.H.S. designations 4D (Primrose Yellow), 5D (Dresden Yellow), 12D (Aureolin) overlaid with 182A, 11B (Straw Yellow), 14C (Lemon Yellow), 22B (Orange Buff), 23D (Cadmium Orange), 24B, 24C (Tangerine Orange), 26C, 26D (Spanish Orange), 34B, 31B (Burnt Orange), 75C-D, 155D (White), 159D overlaid with 186A, 161C overlaid with 182C and 4C overlaid with 70A.

2. A chrysanthemum plant named Pale Pink Snapper of the classification *morifolium ramat* distinguished by having (a) a height of about 99 cm. and a stem diameter of about 6 mm. and being of vigorous and strong upright growth, (b) branching freely with terminal shoots which express buds rapidly under short-day conditions, and (c) having a leaf formation of about one leaf per day in high-light conditions, (d) about a nine-week short-day response to maturity for June flowering at 60° F. night temperature and flowering year around under photoperiod control, (e) the flowers being of daisy capitulum form borne in corymbiform spray clusters and having a fully expanded diameter of about 70 to 80 mm., a coloration of substantially RHS 75C-D, and a chromosome count of 54 with at least one that is telocentric.

3. A *chrysanthemum morifolium* named White Snapper having the characteristics defined by claim 1 wherein the flower stem is about 93 cm. high and its diameter is about 6 mm., the capitulum diameter is about 80 mm. when fully opened and the general coloration is White RHS 155D with a disc color of Scheeles Green RHS 144B.

4. A *chrysanthemum morifolium* named Bronze Snapper according to claim 1 wherein the flower stem is about 87 cm. long with a diameter of about 7 mm., the capitulum is about 80 mm. in diameter when fully opened and the general coloration is Straw Yellow RHS 13C with the disc color being substantially Scheeles Green RHS 144B.

5. A chrysanthemum plant named Salmon Bronze according to claim 1 wherein the flower stem is about 87 mm. long and about 7 mm. in diameter, and the capitulum has a diameter of about 80 mm. with a general coloration of Greyed Yellow RHS 161C overlaid with Greyed Red RHS 182C.

6. A *chrysanthemum morifolium* named Yellow Snapper according to claim 1 wherein the flower stem is about 94 cm. in length and about 6 mm. in diameter, the capitulum is about 80 mm. in diameter with a general coloration of Light Yellow RHS 4D when fully opened, and a disc color of Scheeles Green RHS 144 which becomes Yellow Orange RHS 14C at dehiscence.

7. A *Chrysanthemum morifolium* named Dark Salmon Snapper according to claim 1 wherein the flower stem is substantially 112 cm. in length and about 6 mm. in diameter, the leaves are relatively small, the capitulum is about 75 mm. in diameter when fully opened and has a general coloration of Orange-White RHS 159B overlaid with Greyed Purple RHS 186A.

8. A *chrysanthemum morifolium ramat* named Pale Yellow Snapper according to claim 1 wherein the stem length is about 87 cm., the stem diameter is about 4 mm., the leaves are of relatively small size, and the capitulum has a diameter of substantially 75 mm. with a color of Very Pale Yellow RHS 5D when fully opened.

9. A *chrysanthemum morifolium ramat* named Copper Bronze Snapper according to claim 1 wherein the flower stem is about 91 cm. in length, the stem diameter is about 6 mm., and the capitulum is about 85 mm. in diameter when fully opened with a coloration of Medium Yellow RHS 12D overlaid with Greyed Red RHS 182A.

10. A *chrysanthemum morifolium ramat* name Apricot Snapper substantially as defined by claim 1 wherein the stem length is about 106 cm. and about 7 mm. in diameter, the leaves are relatively large, and the capitulum has a general diameter of about 85 mm. with a ray floret coloration of Greyed Orange RHS 163B overlaid with Red RHS 46A when the flowers are expanding which becomes Yellow RHS 4C lightly overlaid with 70A when the flowerhead is blown.

11. A *chrysanthemum morifolium ramat* named Pale Salmon Snapper substantially as defined by claim 1 wherein the stem length is about 97 cm. with a diameter of about 6 mm., the bud color is Light Orange RHS 27A when the bracts first divide, the ray florets have an outer side color of Yellow RHS 11C and an inner side color of Light Orange RHS 25D when the flowers are expanding which becomes Yellow Orange RHS 23D on the top side when the flowerhead is blown, and the capitulum has a diameter of 85 mm. when fully open.

12. A *chrysanthemum morifolium ramat* named Golden Bronze Snapper substantially as defined by claim 1 wherein the stem length is about 96 cm. and about 5 mm. in diameter, the bud color is Yellow Orange RHS 22A when the bracts divide, the ray florets have an outer side color of Light Yellow Orange 13C and an inner side color of Yellow Orange RHS 23B when the flowers are expanding and a lighter Yellow Orange RHS 22B when the flowerhead is blown, and the capitulum has a diameter of 78 mm. when fully open.

13. A *chrysanthemum morifolium ramat* named Salmon Red Snapper having the characteristics defined by claim 1 wherein the stem length is about 85 cm. with a diameter of about 6 mm., and the capitulum has a diameter of about 80 mm. when the flower is fully opened, the ray floret color being Orange Red RHS 34C on the outer side and RHS 34B on the inner side when the flower is expanding, and when the flowerhead is blown the ray floret top side color is Orange Red RHS 31B.

14. A *chrysanthemum morifolium ramat* named Bright Yellow Snapper having the characteristics set out in claim 1 and wherein the ray florets of the flower are of Yellow Orange RHS 8B on the outer side and Yellow Orange RHS 9A on the inner side when the flower is expanding and having the Yellow color RHS 14C on the top side when the flowerhead is blown, the stem length being 102 cm. with a 6 mm. diameter, and the capitulum having a diameter of 80 mm. when fully open.

15. A *chrysanthemum morifolium ramat* named Dark Golden Bronze Snapper having the characteristics set out in claim 1 and wherein the ray florets are of Middle Yellow RHS 13B on the outer side and Orange RHS 24B on the inner side when the flowers are expanding and a top side lighter Orange color RHS 24C when the flowerhead is blown, the stem length being about 99 cm. with a diameter of about 6 mm., and the capitulum diameter being 85 mm. when fully open.

16. A *chrysanthemum morifolium ramat* named Dark Salmon Bronze Snapper having the characteristics defined by claim 1 wherein the ray florets of the expanding flower are of a Yellow Orange color RHS 19C on the outer side and an Orange color RHS 26C on the inner side, the Orange color of the inner side becoming a much light color RHS 26D when the flowerhead is blown, the stem length is 107 cm. with a diameter of 7 mm., and the capitulum has a diameter of 85 mm. when fully open.

17. Propagating material from a *chrysanthemum morifolium ramat* plant selected from the group consisting of the plant named Pale Pink Snapper and radiation-induced mutants thereof, including the Snapper cultivars generically named White Snapper, Bronze Snapper, Salmon Bronze Snapper, Yellow Snapper, Dark Salmon Snapper, Pale Yellow Snapper, Apricot Snapper, Copper Bronze Snapper, Pale Salmon Snapper, Salmon Red Snapper, Dark Golden Bronze Snapper, Dark Salmon Bronze Snapper and Bright Yellow Snapper.

18. Cut flowers of a *chrysanthemum morifolium ramat* plant selected from the group defined by claim 1.

* * * * *